United States Patent
Farassat

(10) Patent No.: US 6,912,906 B2
(45) Date of Patent: Jul. 5, 2005

(54) METHOD AND APPARATUS FOR THE PRODUCTION AND QUALITY TESTING OF A BONDED WIRE CONNECTION

(75) Inventor: Farhad Farassat, Taufkirchen (DE)

(73) Assignee: F&K Delvotec Bondtechnik GmbH, Ottobrunn (DE)

( * ) Notice: Subject to any disclaimer, the term of this patent is extended or adjusted under 35 U.S.C. 154(b) by 0 days.

(21) Appl. No.: 10/863,554

(22) Filed: Jun. 8, 2004

(65) Prior Publication Data

US 2004/0221653 A1 Nov. 11, 2004

Related U.S. Application Data

(63) Continuation of application No. 10/161,320, filed on May 31, 2002, now Pat. No. 6,745,629.

(30) Foreign Application Priority Data

Mar. 8, 2002 (EP) .............................. 02005435

(51) Int. Cl.$^7$ ............................................... G01N 29/08
(52) U.S. Cl. .............................. 73/588; 73/589; 73/827
(58) Field of Search .......................... 73/588, 589, 600, 73/602, 574, 801, 827, 842, 599; 228/102, 103, 104

(56) References Cited

U.S. PATENT DOCUMENTS

| 4,341,574 A | * | 7/1982 | Landes .................. 156/64 |
| 4,445,378 A | | 5/1984 | Zuckerwar .................. 73/589 |
| 4,619,397 A | | 10/1986 | Urban .................. 228/111 |
| 4,984,730 A | | 1/1991 | Gobel et al. .................. 228/1.1 |
| 5,213,249 A | | 5/1993 | Long et al. .................. 228/102 |
| 5,314,105 A | | 5/1994 | Farassat .................. 228/102 |
| 5,889,210 A | | 3/1999 | Inoue .................. 73/588 |
| 5,894,981 A | * | 4/1999 | Kelly .................. 228/104 |
| 6,308,881 B1 | * | 10/2001 | Hesse et al. .................. 228/102 |
| 6,512,444 B1 | * | 1/2003 | Morris et al. .................. 337/401 |
| 6,568,581 B2 | | 5/2003 | Boller et al. .................. 228/103 |

FOREIGN PATENT DOCUMENTS

| DE | 44 47 073 | 7/1996 |
| GB | 2 271 305 | 4/1994 |

* cited by examiner

Primary Examiner—Hezron Williams
Assistant Examiner—Jacques M. Saint-Surin
(74) Attorney, Agent, or Firm—Knobbe, Martens, Olson & Bear, LLP

(57) ABSTRACT

Method of producing a bonded wire connection between an electronic component or a subassembly and a carrier by introducing energy from an ultrasound transducer into a wire that is to be bonded. According to this method, during the introduction of energy the impedance of the ultrasound transducer is measured as a function of time. The shape of the curve representing this time dependence is evaluated on the basis of a pre-specified comparison criteria, and the power input to the ultrasound transducer and/or a bond weight exerted on the wire is/are controlled in dependence on the result of this evaluation. A device usable for carrying out this method is also described.

18 Claims, 3 Drawing Sheets

METHOD AND APPARATUS FOR THE PRODUCTION AND QUALITY TESTING OF A BONDED WIRE CONNECTION

RELATED APPLICATIONS

This application is a continuation of U.S. application Ser. No. 10/161,320 filed May 31, 2002 (which issued Jun. 8, 2004 as U.S. Pat. No. 6,745,629) and claims the benefit of European application 02 005 435.9 filed Mar. 8, 2002, both of which are herein incorporated by reference in their entireties.

BACKGROUND OF THE INVENTION

1. Field of the Invention

This invention relates generally to wire bonding, and specifically to a method and apparatus for the production and quality control testing of an ultrasonically bonded wire connection.

2. Description of the Related Art

Bonding is an extremely widely used method of connecting wires in electronic devices of all kinds, in order to form contacts with electronic components and in particular integrated circuits (chips). The quality of these connections determines to a considerable extent the performance and reliability of the relevant electronic devices. Therefore the manufacturers of these devices pay great attention to monitoring the quality of the connections, and the manufacturers of wire-bonding machines are faced with a demand for ever more reliable testing and process-control systems.

One of the furthest developed and most widespread bonding methods is ultrasonic ("wedge") bonding, which basically represents a micro-version of friction welding. Here—as described, for example, in the applicant's patent U.S. Pat. No. 4,619,397—an aluminium wire in contact with a substrate surface, to which it is to be connected in such a way that the two materials remain in contact, is put into rapid oscillation by an ultrasound transducer and simultaneously pressed against the surface. Under the influence of the compression (bonding) force and the oscillation (bonding) power, an oxide coating on the surface is broken up and, as severe deformation and local heating occur, the wire and surface materials intermingle to produce bonding at the interface between wire and surface.

A more detailed description of this method is unnecessary here, as it has long been well known to those skilled in the art.

For testing bonded connections produced in this way, many methods have been established, of which reference is made here only to that disclosed in the applicant's patent U.S. Pat. No. 4,984,730. This document describes a test method based on monitoring a deformation of the wire during the bonding process and comparison with a standard or reference curve. When the measured deformation curve is too far from the reference curve, this is regarded as indicating inadequate quality of the bonded connection, and when such unacceptable deviations are detected, the procedure should be interrupted and the relevant process parameters readjusted.

A method of testing connections produced by ultrasonic bonding that is similar, in a certain sense, is described in the patent DE 44 47 073 C1. Here the firmness of the connection is the decisive parameter for the bond quality. It is proposed that the relevant parameter to be monitored is the velocity or time course of deformation of the wire to be bonded and the time course of the amplitude of the bonding tool (wedge amplitude) during the bonding process; the results of this monitoring are to be compared with reference data. This method enables the firmness of each individual connection to be tested with no substantial extra expenditure of time.

In the applicant's patent U.S. Pat. No. 5,314,105 a system is proposed for controlling an ultrasonic wire-banding process in-real time, or quasi-real time, by monitoring the time dependence of deformation of the bonded wire. Specifically, it is proposed that the power input to the ultrasound transducer should be kept at a high level until a marked increase in deformation appears in the time-dependence curve, at which point the power is reduced to a predetermined lower level. Furthermore—in a preferred procedure—it is proposed to turn the ultrasound transducer off completely when the wire deformation has substantially reached a predetermined final value.

In the applicant's patent GB 2 271 305 B a procedure for controlling a soldering or bonding process of the reflow type is proposed, in which the power applied to drive prespecified sections of the process is adjusted to different levels. In this document the application of this principle for a wire bonder of the kind cited above is also mentioned.

The previously proposed methods and apparatus have proved not to provide optimal results in all of the constellations of materials and processes encountered in practice. It has been impossible to control or regulate the bonding process in the initial phase (the first five to ten ms), because during this period the wire to be bonded was not deformed sufficiently to permit evaluation.

SUMMARY OF THE INVENTION

Hence it is the objective of the invention to provide an improved method of this generic kind as well as an apparatus suitable for implementing the method, which enable a further improvement in ensuring the quality of bonded wire connections.

The invention includes the fundamental idea of monitoring, by means of a suitable parameter, a reaction of the bonding process upon the tool—the ultrasound transducer—and thereby detecting a substantial change of state of the work piece, namely the wire-substrate unit during formation of the bonded connection. It further includes the idea of utilizing as this parameter the impedance measured at the transducer. Finally, the invention includes the idea of comparing the recorded time dependence of the representative parameter (impedance) with a suitable reference, which is obtained during the manufacture of qualitatively perfect bonded connections.

The-invention enables an improved control or regulation of the bonding process, in particular in its initial phase, because a quantity which has an informative time-dependence during this phase is used as an input variable for the control and regulation process.

In a first, relatively independent implementation of the idea behind the invention, the proposed method is a manufacturing procedure insofar as it comprises, in addition to the above-mentioned aspects, the concept of controlling the power input to the ultrasound transducer (the bond power) or the force that the bonding tool exerts on the wire (bond weight), or both of these variables.

In a second implementation of the idea behind the invention, the proposed method represents a test procedure for quality control of the bonded connection that is produced, insofar as it allows the decision as to quality of the bonded connection to be derived from the recorded time dependence of the impedance in comparison to the reference curve.

The inventor has established, on the basis of extensive experimental investigations, that a particular characteristic shape of the impedance-time curve, distinguished by a relatively steep rise to a clear maximum and a subsequent decline, initially steeper and then becoming less steep, can be taken as an unambiguous indicator of a qualitatively high-value connection. It will be evident that for different bonding-process parameters, in particular for wires differing in composition and dimensions as well as substrate surfaces of various kinds, the specific time dependence of the impedance and in particular the position of the maximum and the rise and fall gradients are different. However, for each constellation of process parameters suitable reference curves can be constructed with a limited number of experiments, which can be used for comparison with a time-dependence curve obtained for the ongoing process.

Evaluation of the curve shape for controlling or regulating the bonding process is preferably carried out by comparison of the overall time dependence recorded while the bonded connection is being produced, or else only a characteristic section of the overall curve, with a reference curve or a set of reference curves. A significant assessment of the quality of the bonded connection is provided, as far as can be seen at present, by evaluation including three predetermined impedance-time reference surfaces (in the following termed "reference windows"), through which the recorded curve representing the time dependence of impedance must pass in order to justify the conclusion that the bonded connection is of high quality.

Alternative possibilities that can be considered in principle include a numerical evaluation of characteristic curve sections—for example, to determine the peak impedance value and a slope of the falling flank in a region of the curve next to the maximum—and numerical comparison with corresponding values obtained from reference measurements. It will be evident that with such a method of evaluation, as well, certain tolerance values with respect to the reference curves should be specified in order for the bonded connection currently being produced to qualify as "good".

In an especially preferred embodiment of the proposed production and/or testing method, the proposed evaluation of the impedance-time curve is combined with an evaluation of the time dependence of the deformation of the wire being bonded (which as such is fundamentally known from the patent U.S. Pat. No. 5,314,105). In particular, the previously known idea of a steplike reduction of the bond power at the time when there is a distinct increase in wire deformation is combined with the idea in accordance with the invention that the bond power and/or bond weight is/are to be controlled in dependence on the characteristic curve for time dependence of the transducer impedance. In analogy, from the combined evaluation of the two time dependences—each in comparison to a reference curve obtained from bonded connections known to be of good quality—an especially reliable decision can be made regarding the quality of the bonded connection.

As also happens when the quality test or process control is based exclusively on the impedance-time dependence, here the quality test or process control on the basis of a combined evaluation of the impedance-time curve and deformation-time curve is in practice preferably automatic, for which purpose at least components of a regulation sequence or system are provided. This regulation component has a special character in the case of the combined method, because the impedance detected at the transducer and the bond power fed into the transducer are originally physically related to one another, and this relationship is in a certain sense "modulated" during the process of producing the bonded connection. This relationship provides a physical basis for the said regulation component.

Aspects of the apparatus for implementing the method correspond to the above-mentioned procedural steps and aspects in a way readily discernible by a person skilled in the art, so that it is not necessary to discuss in detail all the components of the apparatus. However, it should be pointed out that an arrangement provided for quality testing comprises, according to the above description, a decision-making device connected to the evaluation device, to compare the impedance-time curve with suitable references and report a good/bad decision. In an arrangement provided for bonding-process control, on the other hand, the evaluation unit is connected to a bond-power control unit and/or bond-weight control unit, which it controls according to a prescribed control algorithm (which has been derived from experimental findings).

BRIEF DESCRIPTION OF THE DRAWINGS

Further advantages and useful features of the invention will be apparent from the following description of preferred exemplary embodiments of the invention with reference to the figures, wherein.

DETAILED DESCRIPTION OF THE PREFERRED EMBODIMENT

Figure 1A:
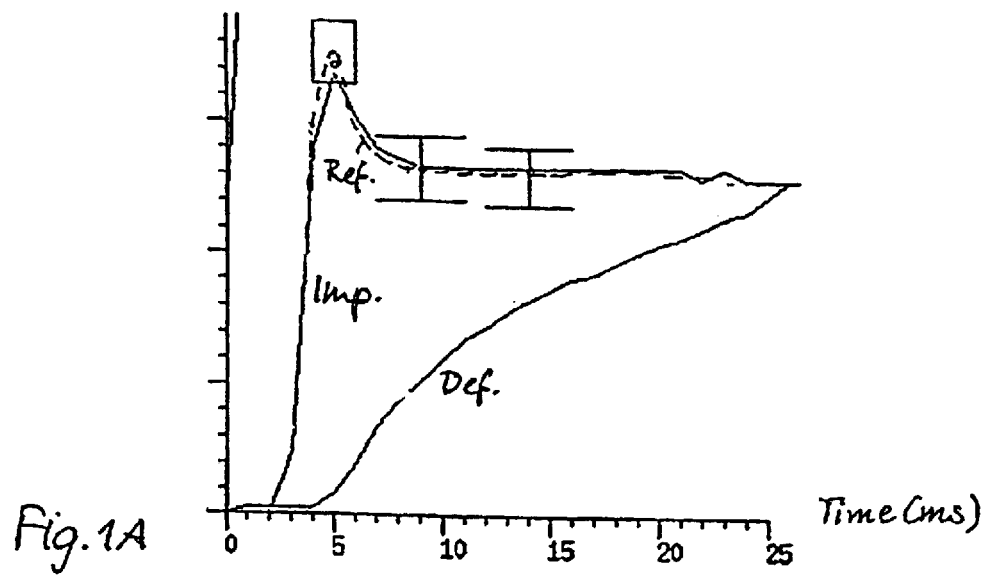
FIGS. 1A, 1B, and 1C are graphs of the time dependence of the impedance of the transducer and the deformation of the bonding wire with reference windows for evaluating the impedance-time curve.
Figure 1B:
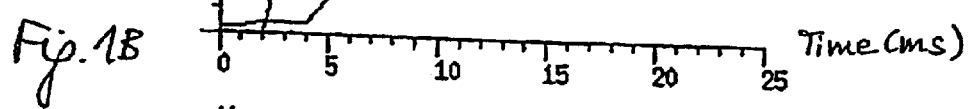
Figure 1C:
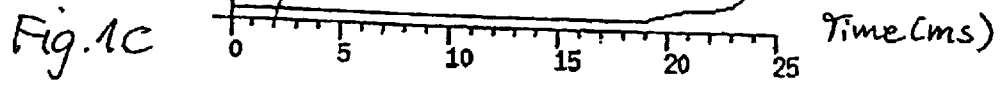

FIGS. 1A, 1B, and 1C show three examples of impedance-time curves and deformation-time curves recorded from a wire bonder; the impedance-time curve is accompanied by a reference curve (dashed line) and three reference windows obtained from prior experimental tests. These identify a process that is proceeding satisfactorily and will produce a high-quality bonded connection.

It is evident that the impedance-time curve in FIG. 1A, with a distinct maximum at ca. 5 ms followed by a steep and then less steep decline, is close to the reference curve, within a narrow tolerance range, and passes through all three time windows. In contrast, the peak of the curve in FIG. 1B does not reach the first window, the next part is also below the second window, and the curve as a whole is relatively far below the reference curve. The curve according to FIG. 1C does pass through the first reference window but not the second and third, and practically its entire course beyond the 6-ms point is above the tolerance range of the reference curve. In the sense of the method proposed here, the bonded connection with a time dependence as shown in FIG. 1A should be evaluated as good, whereas bonded connections, during the production of which the time dependences of impedance according to FIG. 1B or 1C were measured, should be judged not good.

The impedance curve according to FIG. 1A is the result of a correctly controlled process.

Figure 2:
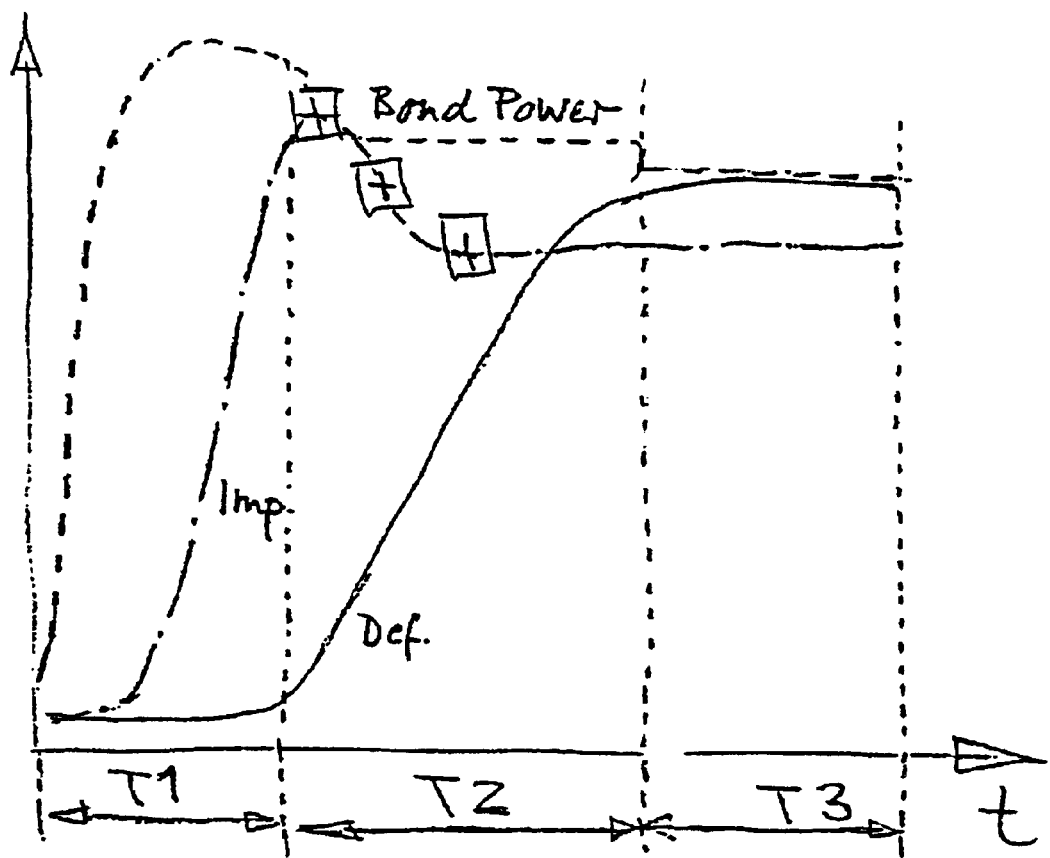
FIG. 2 is a synoptic representation of the time dependence of impedance and deformation and of suitably controlled bond power, with identification of characteristic time spans.

FIG. 2 shows typical time dependences of the impedance of the transducer and the deformation of the bonded wire in a synoptic diagram, including a (controlled) time dependence of the bond power. The time span T1, until the deformation-time curve begins to rise sharply and the impedance-time curve approaches its maximum, is a span during which the transducer-induced oscillation of the wire on the substrate surface causes cleaning of the latter. During the time span T2 the materials of which the wire and the substrate are made become intermingled; that is, the actual welding occurs, while the cleaning process continues. In the time span T3 a tempering of the welded connection occurs under the action of the heat that is generated.

Hence it is reasonable for the bond power to be controlled in three stages, the first of which involves a stepwise reduction depending on monitoring of the time dependence of the impedance at time point T1. The next is a second stepwise reduction depending on the evaluation of the time dependence of deformation at time point T2, and at time point T3 the bonding process can be terminated.

Figure 3:
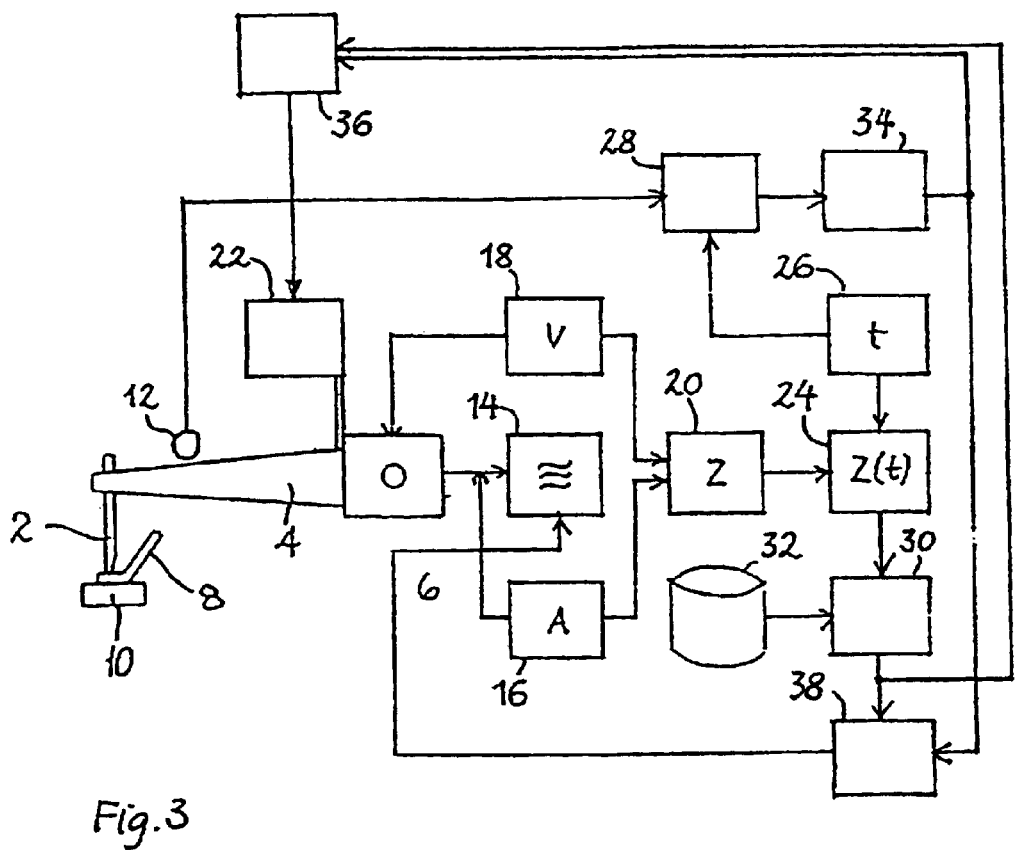
FIG. 3 is a block diagram to show the function of a first arrangement to carry out the method in accordance with the invention.

FIG. 3 is a diagram of an arrangement 1 to carry out a bonding process controlled in dependence on the impedance-time curve, which can be integrated into a wire bonder (not shown as a whole). Of the usual components of a wire bonder, those represented here are a bonding tool 2, which is attached to the horn 4 of an ultrasound transducer 6 and serves to produce a bonded connection between a wire 8 and a substrate 10.

Associated with the horn 4 of the ultrasound transducer 6 is a deformation sensor 12 that is known per se. Integrated into a power supply 14 of the transducer 6 are a device 16 to measure the strength of the electrical current and a device 18 to measure the voltage; these are connected at their output sides to an impedance-determining device 20, which calculates the momentary impedance values. Another component associated with the transducer 6 is a bonding-head driver 22, which generates a predetermined pressing force (bond weight) that the bonding tool 2 exerts on the wire 8. To the output of the impedance-determining device 20 is connected an impedance-recording device 24, to record the time dependence of the impedance, and this in turn is connected by way of an additional input to a timer 26. The deformation sensor 12 is connected to the input of a deformation-recording device 28 to record the time dependence of the wire deformation, and this device likewise receives a time signal from the timer 26.

The impedance-recording device 24 is connected at its output to an impedance-evaluating device 30, which by way of another input is connected to a reference database 32. The output of the deformation-recording device 28 is connected to a deformation-evaluating device 34. Both of the evaluating devices 30 and 34 are together connected on one hand to a bond-weight control unit 36 and on the other hand to a bond-power control unit 38. The bond-weight control unit 36 acts on the bonding-head driver 22 so as rapidly to control the bond weight, and the bond-power control unit 38 acts on the power supply 14 of the transducer 6 so as rapidly to adjust the bond power (ultrasound-oscillation energy).

The way in which the measurement and control arrangement 1 functions will be evident from the above general explanations of the proposed method and hence will not be described further here. It should be pointed out that in the evaluating devices 30 and 34 and the control units 36 and 38, evaluation and control algorithms, respectively, are stored which have been derived from curves for transducer impedance and wire deformation obtained by experiments on a plurality of substrates with various kinds of wires and constellations of procedural parameters, along with the quality studies customarily associated therewith. Such measurements and quality tests are familiar to experts in bonding techniques, who can thus find for themselves specific control algorithms for specific structural elements, substrates and bond wires.

Figure 4:
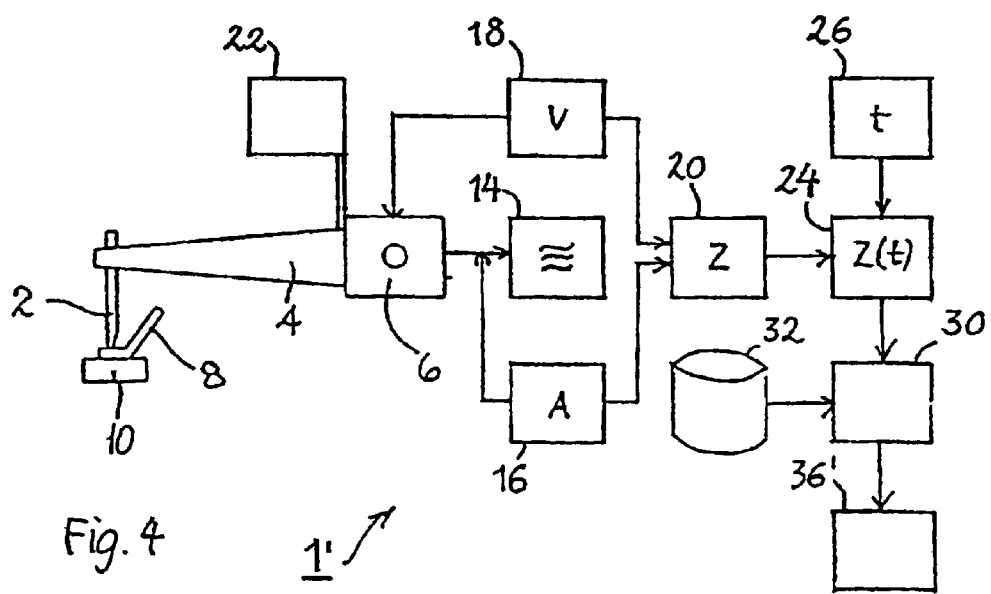
FIG. 4 is a block diagram to show the function of a second arrangement to carry out the method in accordance with the invention.

FIG. 4 shows a test arrangement 1', which is considerably simpler than the measurement and control arrangement 1 according to FIG. 3. Here a wire bonder with the customary structure—again, the only elements thereof shown in the drawing are the bonding tool 2, the horn 4, the transducer 6 and the bonding-head driver 22—comprises in addition only the current-measurement device 16, the voltage-measurement device 18, and the impedance-determining device 20 plus the impedance-recording device 24 and impedance-evaluating device 30 with associated database 32. Of the elements shown in FIG. 3, those that are no longer present are the means of detecting and evaluating deformation and of controlling the bonding process. Instead, the impedance-evaluating device 30 here is connected at its output to a decision stage 36', which sends out a "good" or "bad" signal to indicate the quality of the bonded connection.

Again, the function of this test arrangement in accordance with the invention will be evident from the above explanations of the proposed method.

The implementation of the invention is not limited to the examples sketched out here but can likewise be achieved in a great many modifications that are within the competence of a person skilled in the art. In particular, the invention also includes control of the bonding process and an apparatus suitable for executing such control, with the provision that either only the bond weight or only the bond power is controlled on the basis of a combined evaluation of the transducer impedance and wire deformation. Also within the scope of the invention are a test method and a test apparatus such that these two parameters are monitored and subjected to combined evaluation in order to make the "good" vs. "bad" decision. Furthermore, the invention includes an implementation in which both the bond weight and the bond power are controlled exclusively on the basis of detection and evaluation of the transducer impedance.

What is claimed is:

1. An apparatus for testing wire bonds formed with a wire bonder having a bonding tool and an ultrasound transducer, the apparatus comprising:

an electrical impedance sensor in communication with the transducer so as to sense the impedance of the transducer;

a deformation sensor in communication with the bonding tool so as to sense the deformation of the wire bonds; and an evaluating device in communication with the impedance sensor and the deformation sensor wherein the evaluating device evaluates the impedance and deformation throughout the bonding process and automatically evaluates the quality of the bonds in process wherein the evaluating device compares the impedance and deformation over time to determine the quality of the bonds and wherein a good quality bond is defined at least partially by a concave up inflection of the impedance occurring within a threshold window of a concave down inflection of the deformation.

2. The apparatus of claim 1, wherein a good quality bond is defined at least partially by a peak of the impedance occurring within a threshold window of a substantial increase of the deformation.

3. The apparatus of claim 1, wherein the evaluating device provides control signals to the wire bonder to indicate a first time interval corresponding generally to a peak of the impedance and a substantial increase in the deformation, a second time interval corresponding generally to the deformation reaching a threshold, and a third time interval corresponding to termination of the bonding process.

4. The apparatus of claim 1, wherein the evaluating device provides control signals to the wire bonder to induce the wire bonder to adjust at least one of a bond weight applied by the bonding tool and a bond power provided to the ultrasound transducer as a function of the evaluation of the impedance and deformation throughout the bonding process.

5. The apparatus of claim 1, wherein a good quality bond is defined by the impedance existing within at least one threshold window.

6. The apparatus of claim 5, wherein a good quality bond is defined by the impedance existing within a plurality of threshold windows wherein the plurality of threshold windows encompass differing impedance ranges.

7. The apparatus of claim 1, further comprising at least one recording device in communication with at least one of the impedance and deformation sensors such that the at least one recording device can record information related to data sensed by the at least one of the impedance and deformation sensors respectively.

8. A wire bonder comprising:
  a bonding tool applied at a bonding weight for forming wire bonds;
  an ultrasound transducer actuated at a bond energy for forming the wire bonds;
  an electrical impedance sensor in communication with the transducer so as to sense the impedance of the transducer;
  a deformation sensor in communication with the bonding tool so as to sense the deformation of the wire bonds; and
  an evaluating device in communication with the impedance sensor and the deformation sensor wherein the evaluating device evaluates the impedance and deformation throughout the bonding process and automatically evaluates the quality of the bonds in process wherein the evaluating device compares the impedance and deformation over time to determine the quality of the bonds and wherein a good quality bond is defined at least partially by a concave up inflection of the impedance occurring within a threshold window of a concave down inflection of the deformation.

9. The apparatus of claim 8, wherein a good quality bond is defined at least partially by a peak of the impedance occurring within a threshold window of a substantial increase of the deformation.

10. The apparatus of claim 8, wherein the evaluating device provides control signals to indicate a first time interval corresponding generally to a peak of the impedance and a substantial increase in the deformation, a second time interval corresponding generally to the deformation reaching a threshold, and a third time interval corresponding to termination of the bonding process.

11. The apparatus of claim 8, wherein the evaluating device provides control signals to adjust at least one of the bond weight and the bond power provided as a function of the evaluation of the impedance and deformation throughout the bonding process.

12. The apparatus of claim 8, wherein a good quality bond is defined by the impedance existing within at least one threshold window.

13. The apparatus of claim 12, wherein a good quality bond is defined by the impedance existing with a plurality of threshold windows wherein the plurality of threshold windows encompass differing impedance ranges.

14. The apparatus of claim 8, further comprising at least one recording device in communication with at least one of the impedance and deformation sensors such that the at least one recording device can record information related to data sensed by the at least one of the impedance and deformation sensors respectively.

15. An apparatus for testing wire bonds formed with a wire bonder having a bonding tool and an ultrasound transducer, the apparatus comprising:
  an electrical impedance sensor in communication with the transducer so as to sense the impedance of the transducer;
  a deformation sensor in communication with the bonding tool so as to sense the deformation of the wire bonds; and
  an evaluating device in communication with the impedance sensor and the deformation sensor wherein the evaluating device evaluates the impedance and deformation throughout the bonding process and automatically evaluates the quality of the bonds in process wherein the evaluating device provides control signals to the wire bonder to indicate a first time interval corresponding generally to a peak of the impedance and a substantial increase in the deformation, a second time interval corresponding generally to the deformation reaching a threshold, and a third time interval corresponding to termination of the bonding process.

16. An apparatus for testing wire bonds formed with a wire bonder having a bonding tool and an ultrasound transducer, the apparatus comprising:
  an electrical impedance sensor in communication with the transducer so as to sense the impedance of the transducer;
  a deformation sensor in communication with the bonding tool so as to sense the deformation of the wire bonds; and
  an evaluating device in communication with the impedance sensor and the deformation sensor wherein the evaluating device evaluates the impedance and deformation throughout the bonding process and automatically evaluates the quality of the bonds in process wherein a good quality bond is defined by the impedance existing within a plurality of threshold windows wherein the plurality of threshold windows encompass differing impedance ranges.

17. A wire bonder comprising:
  a bonding tool applied at a bonding weight for forming wire bonds;
  an ultrasound transducer actuated at a bond energy for forming the wire bonds;
  an electrical impedance sensor in communication with the transducer so as to sense the impedance of the transducer;
  a deformation sensor in communication with the bonding tool so as to sense the deformation of the wire bonds; and an evaluating device in communication with the impedance sensor and the deformation sensor wherein the evaluating device evaluates the impedance and deformation throughout the bonding process and automatically evaluates the quality of the bonds in process wherein the evaluating device provides control signals to indicate a first time interval corresponding generally to a peak of the impedance and a substantial increase in the deformation, a second time interval corresponding generally to the deformation reaching a threshold, and a third time interval corresponding to termination of the bonding process.

18. A wire bonder comprising:

a bonding tool applied at a bonding weight for forming wire bonds;

an ultrasound transducer actuated at a bond energy for forming the wire bonds;

an electrical impedance sensor in communication with the transducer so as to sense the impedance of the transducer;

a deformation sensor in communication with the bonding tool so as to sense the deformation of the wire bonds; and an evaluating device in communication with the impedance sensor and the deformation sensor wherein the evaluating device evaluates the impedance and deformation throughout the bonding process and automatically evaluates the quality of the bonds in process wherein a good quality bond is defined by the impedance existing with a plurality of threshold windows wherein the plurality of threshold windows encompass differing impedance ranges.

* * * * *